United States Patent [19]

LeCocq

[11] Patent Number: 4,553,958
[45] Date of Patent: Nov. 19, 1985

[54] IV DELIVERY CONTROLLER

[75] Inventor: Andrew D. LeCocq, Columbia, Md.

[73] Assignee: Quest Medical, Inc., Carrollton, Tex.

[21] Appl. No.: 463,976

[22] Filed: Feb. 4, 1983

[51] Int. Cl.⁴ .............................................. A61M 5/16
[52] U.S. Cl. ...................................... 604/67; 604/81;
604/246; 128/DIG. 13
[58] Field of Search ................ 128/DIG. 13; 604/50,
604/49, 65–67, 80, 81, 245, 246; 73/861.41;
364/147, 710, 706; 222/25–29, 41, 42

[56] References Cited
U.S. PATENT DOCUMENTS

| | | | |
|---|---|---|---|
| 3,985,133 | 10/1976 | Jenkins et al. | 604/67 |
| 4,094,318 | 6/1978 | Burke et al. | 604/81 |
| 4,207,871 | 6/1980 | Jenkins | 128/214 R |
| 4,247,901 | 1/1981 | Martin et al. | 364/147 |
| 4,265,240 | 5/1981 | Jenkins | 128/214 E |
| 4,316,460 | 2/1982 | Genese et al. | 128/214 R |
| 4,324,238 | 4/1982 | Genese et al. | 128/214 G |
| 4,391,598 | 7/1983 | Thompson | 128/DIG. 13 |

OTHER PUBLICATIONS

"New Concepts in Intermittent I.V. Therapy by Travenol Lab., Inc.", Life Care Pump Tips/2 by Abbott Labs. "Design Goal: Simple Perfection in I.V. Flow Control", Continu–Flow Administration Set, (p. 2).
National Intravenous Therapy Association, (vol. 4, No. 1, pp. 9–14).

Primary Examiner—William E. Kamm
Assistant Examiner—Steven Falk
Attorney, Agent, or Firm—Richards, Harris, Medlock & Andrews

[57] ABSTRACT

A controller (34) is disclosed for use with a dual delivery system including a primary fluid container (12) and a secondary fluid container (14). The display (48) on the controller (34) presents a representation of the primary and secondary containers and prompts the operator to input the desired primary and secondary fluid flow rates and primary and secondary fluid volumes to be infused. During operation of the controller, a series of flow lines displays (118, 126, 144) represent motion of fluid from the container being drained to indicate to the operator which fluid is being infused. An alarm will be sounded upon the detection of an occlusion within the flow lines, the presence of air within the flow lines or an open door on the controller. During the flow from a particular container, the displays associated with the other container are deactivated to prevent confusion to the operator.

31 Claims, 12 Drawing Figures

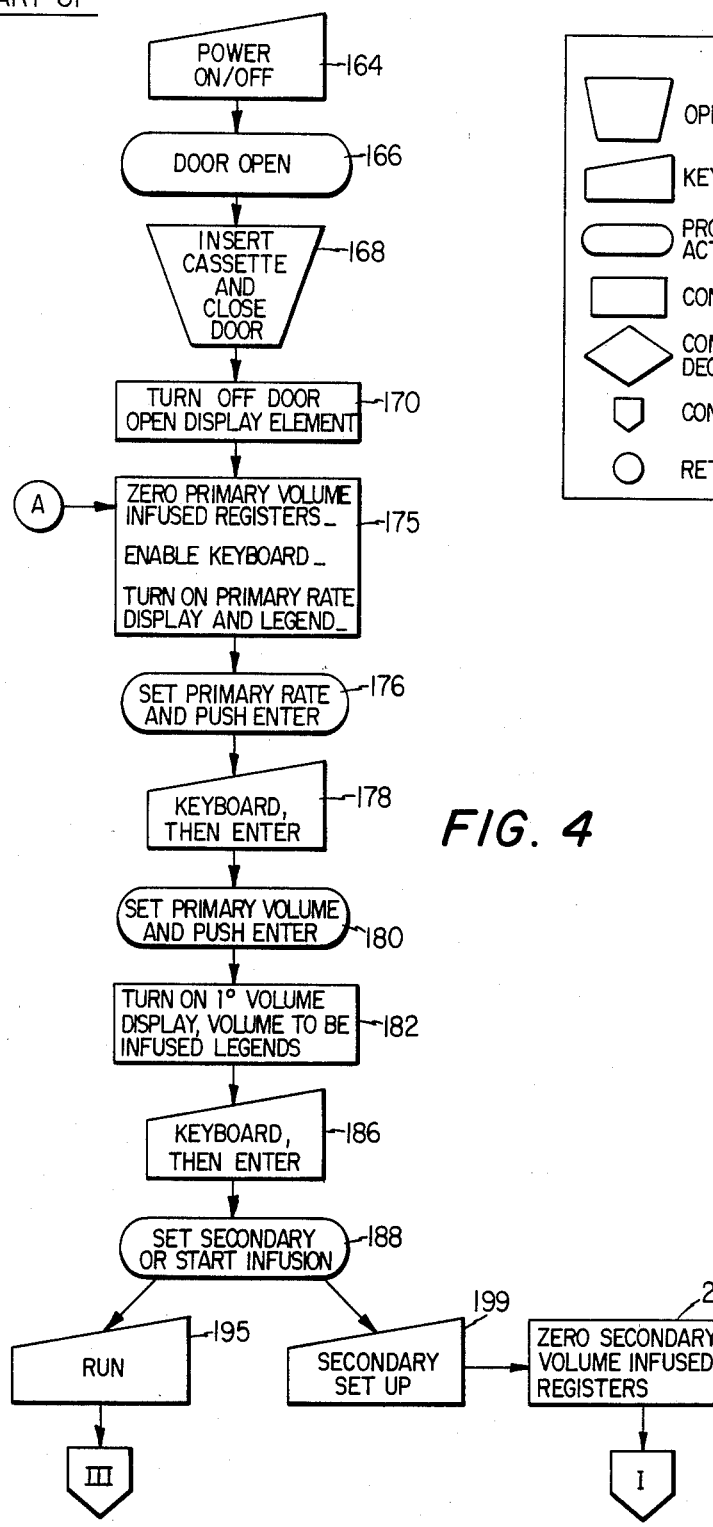
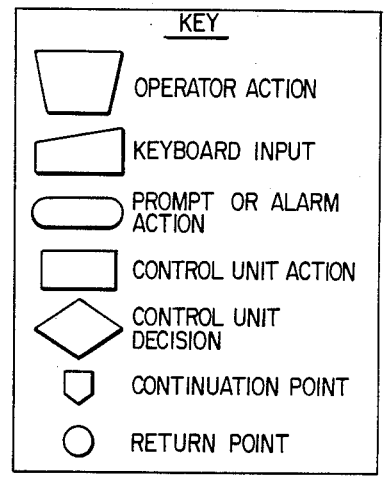
FIG. 4

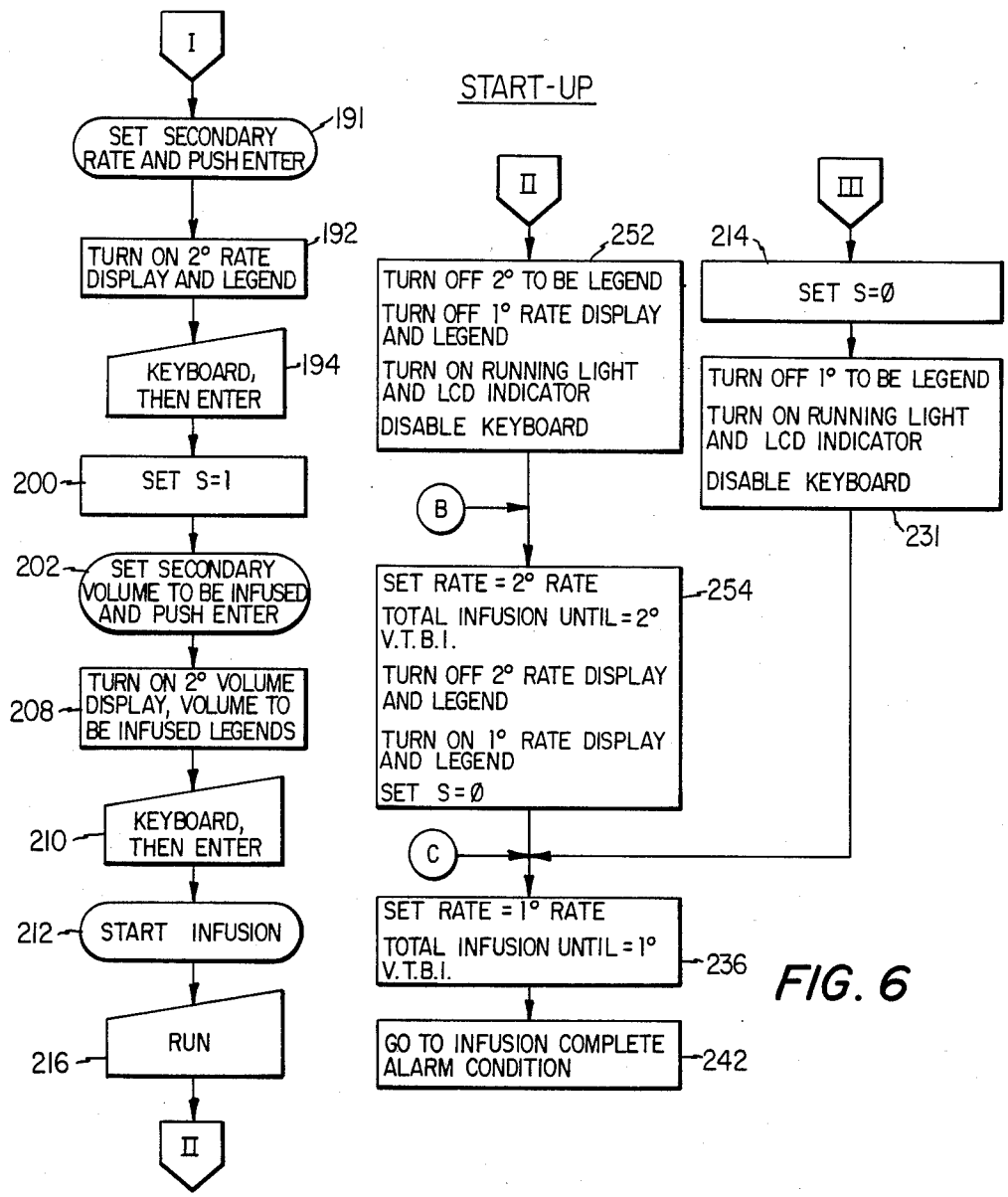

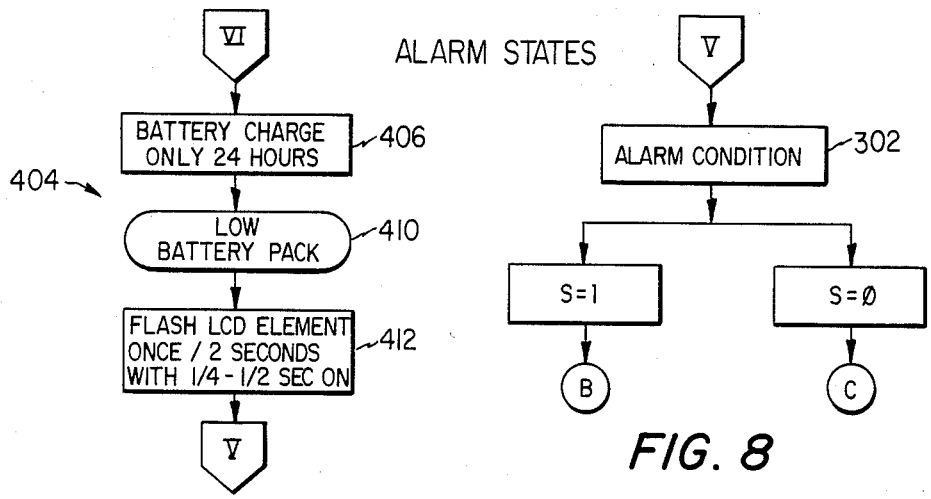
FIG. 7C
FIG. 8
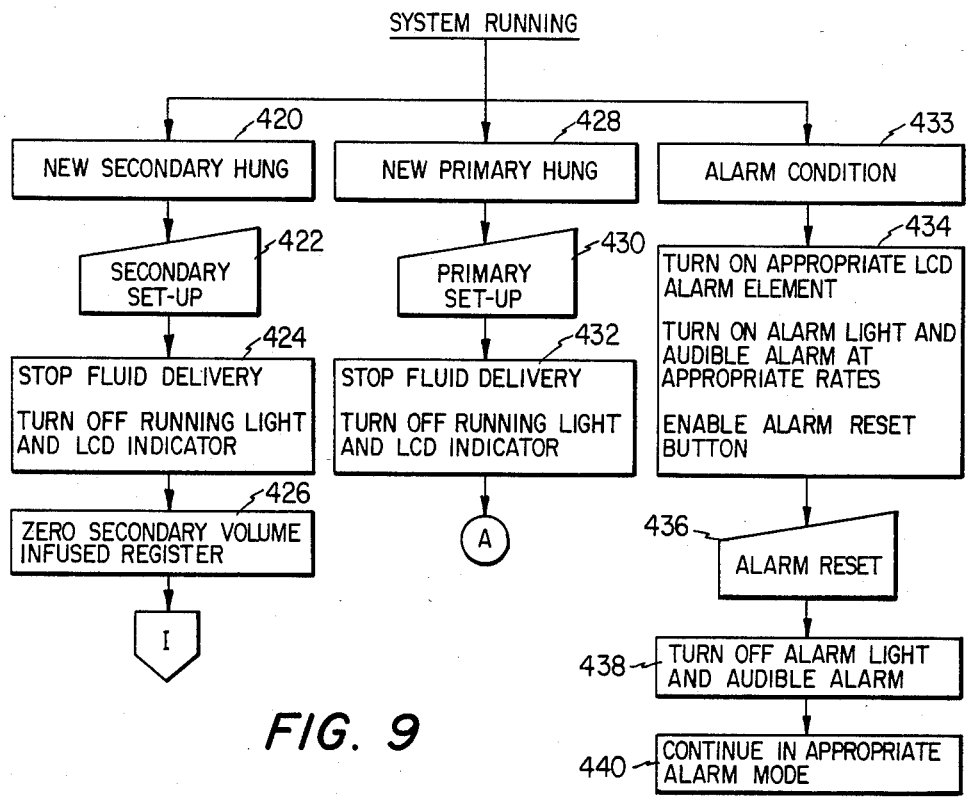
FIG. 9

IV DELIVERY CONTROLLER

TECHNICAL FIELD

This invention relates to the intravenous delivery of fluids to a patient, and in particular to a controller permitting fluid delivery of either one or two fluids at predetermined rates to infuse predetermined volumes.

BACKGROUND ART

In medical care, it is often necessary to infuse fluids into a patient through intravenous delivery (IV). These fluids can comprise, for example, nutritional fluids and drugs, such as antibiotics. In a common application, a primary container is provided which holds a volume of a primary fluid, such as a nutrient. A secondary container is also provided, containing a secondary fluid. The secondary fluid is commonly a drug or medicament.

Fluid flow lines extend from each of the containers to a Y-connection beneath the containers. A check valve or another one-way flow device is positioned in the flow line from the primary container between the primary container and Y-connection.

The secondary container is maintained at an elevation above the primary container. Therefore, the hydrostatic pressure of the secondary fluid is sufficient to close the check valve in the primary fluid flow line and block flow from the primary container until the secondary container is empty. When the secondary fluid has been infused, the check valve will open, permitting infusion of the primary fluid.

In the past, a number of techniques have been employed to control the rate of infusion of the primary and secondary fluids. Controlled drip chambers have been mounted on each container with the flow rate being calculated by the quantity of drops falling into the chamber per unit time. Positive pressure pumps have been used to pump the fluid from the containers to the patient. U.S. Pat. No. 4,265,240, issued May 5, 1981 to Jenkins discloses the use of two pumps, one in each fluid line, to infuse the fluids. Attempts have also been made to incorporate a flow control device in an IV delivery system operating by the hydrostatic pressure of the fluid. One device of this type is disclosed in U.S. Pat. No. 4,204,538, issued May 27, 1982 to Cannon. However, none of these devices have been totally effective.

In any IV delivery system, critical factors that must be recognized are the necessity to design the delivery system so that the system can be operated with a minimum of effort and training and the necessity to minimize opportunities for the operator to incorrectly set the infusion conditions. The nurse, or other operator, must be able to thoroughly understand the procedure to establish the desired flow. In addition, the procedure to set the desired flow rates should be designed to occupy the minimum of the nurse's time. Therefore, a delivery system is needed which permits the nurse to thoroughly understand the procedure for initiating and setting flow rates. A need exists also for a controller having a display which will be readily understood by operating personnel at all stages of operation of a delivery system for providing highly accurate flow control for a primary and a second fluid or, in an alternate mode of operation, a single fluid.

SUMMARY OF THE INVENTION

This invention contemplates a method and apparatus for a controller used in intravenous infusions of a single fluid or infusions of a primary fluid from a primary container and a secondary fluid from a secondary container in which the secondary fluid is delivered at a first predetermined rate until a preselected volume or time of delivery has occurred and the primary fluid is subsequently delivered at a second predetermined rate. Container display means provide a visible representation of both the primary and secondary containers, and infusion data display means can display a first display in association with the representation of the secondary container showing the first predetermined rate of instantaneous infusion data for fluid infused at that rate. The display means can also produce a second display, in association with the visible representation of the primary container, showing the second predetermined rate and instantaneous infusion data for delivery at the second rate. Instantaneous infusion data for a given rate may be, for example, the volume delivered at that rate at the time of display. Flow activation display means are provided to generate a visible indication of the activation of flow from each container to the patient.

In the preferred embodiment only the first display is produced during infusion at the first rate, and only the second display is produced during infusion at the second rate. Prompting means are provided in the controller for sequentially prompting the operator to select desired infusion data for each fluid in them. Infusion data may be specified by any two of: time, rate and volume. In the preferred embodiment, each container representation encompasses the display of the infusion data pertaining to its fluid.

BRIEF DESCRIPTION OF THE DRAWINGS

A more complete understanding of the invention and its advantages will be apparent from the following Detailed Description when taken in conjunction with the accompanying Drawings, in which:

FIGS. 4, 5 and 6 are flow charts representing the logic of the controller under normal operation;

FIGS. 7A, 7B, 7C and 8 are flow charts representing the logic of the controller in an alarm condition; and FIG. 9 is a flow chart representing the logic of the controller in a reset condition subsequent to completion of infusion or an alarm condition.

DETAILED DESCRIPTION

Figure 1:
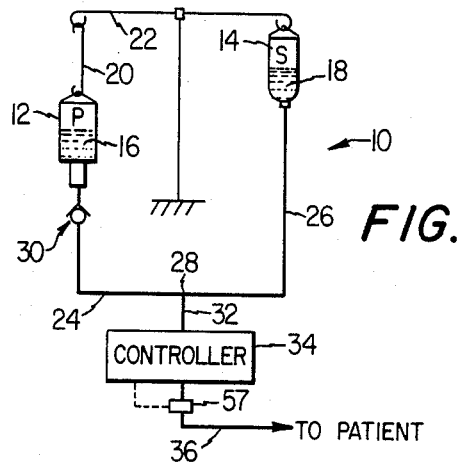
FIG. 1 illustrates a fluid delivery system having primary and secondary fluid containers incorporating a controller forming a first embodiment of the present invention.

Referring now to the Drawings, wherein like reference characters designate like or corresponding parts throughout several views, an IV delivery system 10 is illustrated in FIG. 1. The IV delivery system includes a primary container 12 and a secondary container 14. The primary container 12 contains a quantity of a primary fluid 16, such as a nutritional fluid. The secondary container contains a secondary fluid 18, such as an antibiotic.

The secondary container 14 is suspended above the primary container 12 by hanging the primary container 12 from a rod 20 off of stand 22. A primary fluid line 24 extends from the primary container 12. A secondary fluid line 26 extends from the secondary container 14. The lines 24 and 26 merge at Y-connection 28. A check valve 30 is positioned in the primary fluid line 24 to prevent back flow towards the primary container. This check valve 30 also insures that the secondary fluid will be infused first by gravity flow as the secondary fluid pressure maintains the check valve closed while secondary fluid 18 remains in the secondary container 14. Once the secondary container 14 has emptied, the check valve 30 will open, permitting infusion of the primary fluid from the primary container 12.

A fluid line 32 extends from the Y-connection 28 into controller 34. A fluid line 36 extends from the controller 34 to the patient. The controller 34 acts to meter fluid from the primary and secondary containers at a rate and volume to be determined by the operator as described in greater detail hereinafter.

Figure 2A:
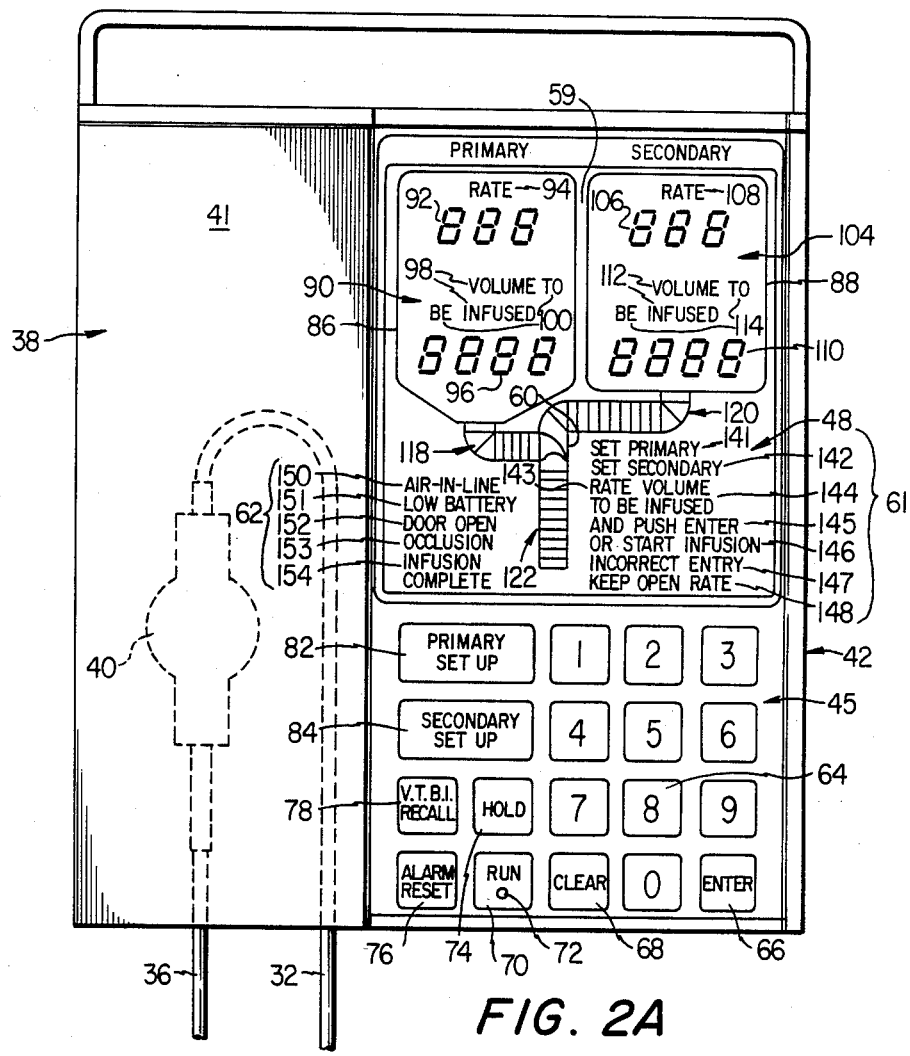
FIG. 2A illustrates the controller and the display panel thereon.

With reference now to FIG. 2A, the controller 34 is illustrated in greater detail. The controller 34 includes a cassette section 38 for holding a metering cassette 40, and a display section 42 for input and display of information.

The fluid lines 32 and 36 attach to the cassette 40. The cassette 40 includes a flexible diaphragm therein and two separate flow paths therethrough. The cassette 40 and activating structure in controller 34 act to meter a predetermined amount of fluid at a variable selected flow rate. A door 41 closes cassette section 38 when the controller is in operation. The details of the cassette and controller operating structure are described in copending U.S. patent applicaion Ser. No. 404,811, filed Aug. 3, 1982 for a Volumetric Metering Unit for Intravenous Fluid Addition, application Ser. No. 258,361, filed Apr. 28, 1981, for an Intravenous Drug Additive Delivery System with Electronic Control and application Ser. No. 258,362, filed Apr. 28, 1981, for a Flow Fault Sensing System, the disclosure of each of which is hereby incorporated by reference as if fully disclosed and set forth herein.

Figure 3:
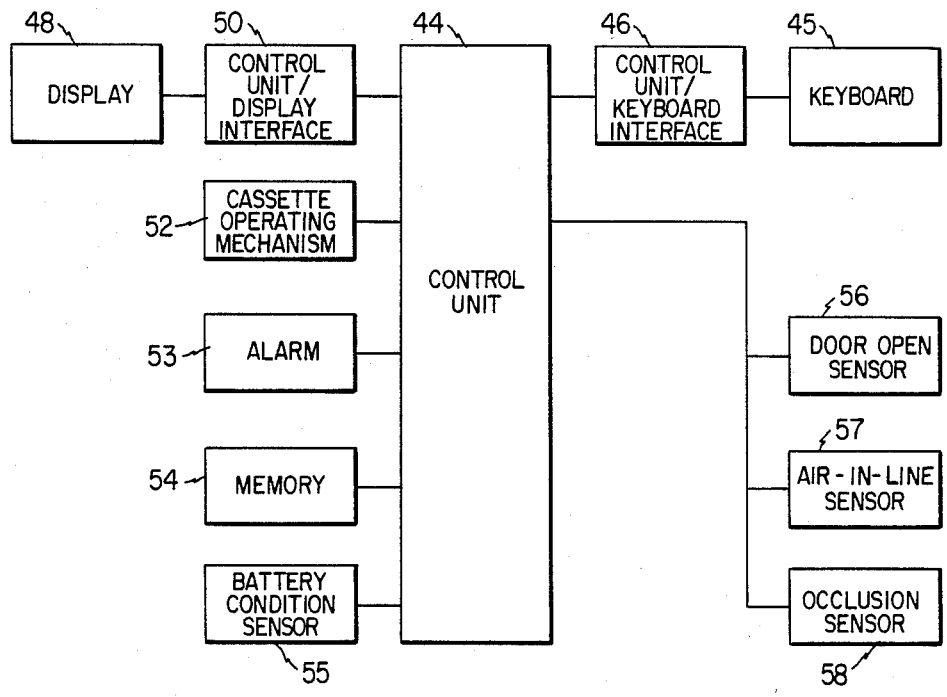
FIG. 3 illustrates a block diagram of the internal electronic components of the controller.
Figure 7A:
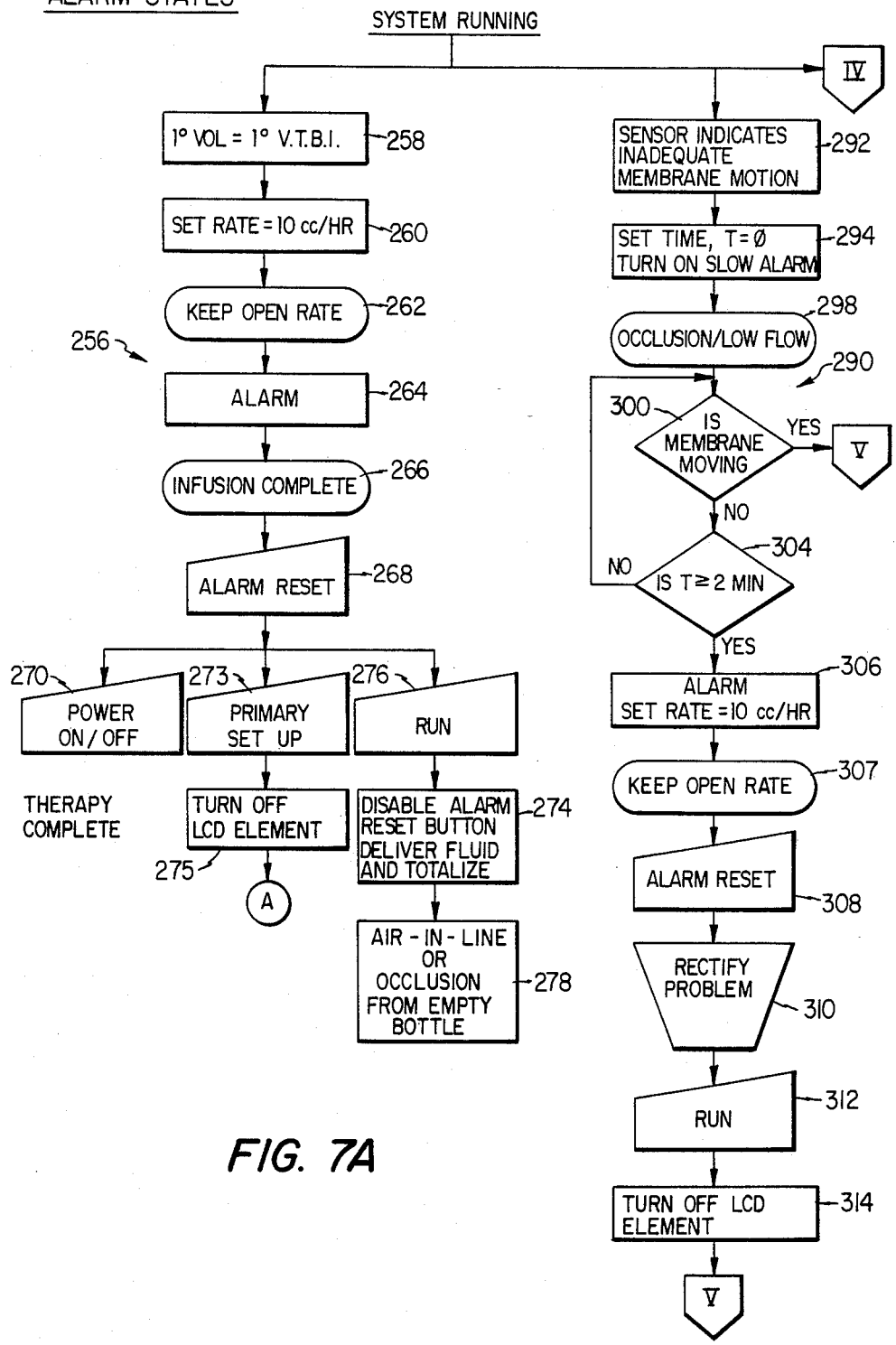
Figure 7B:
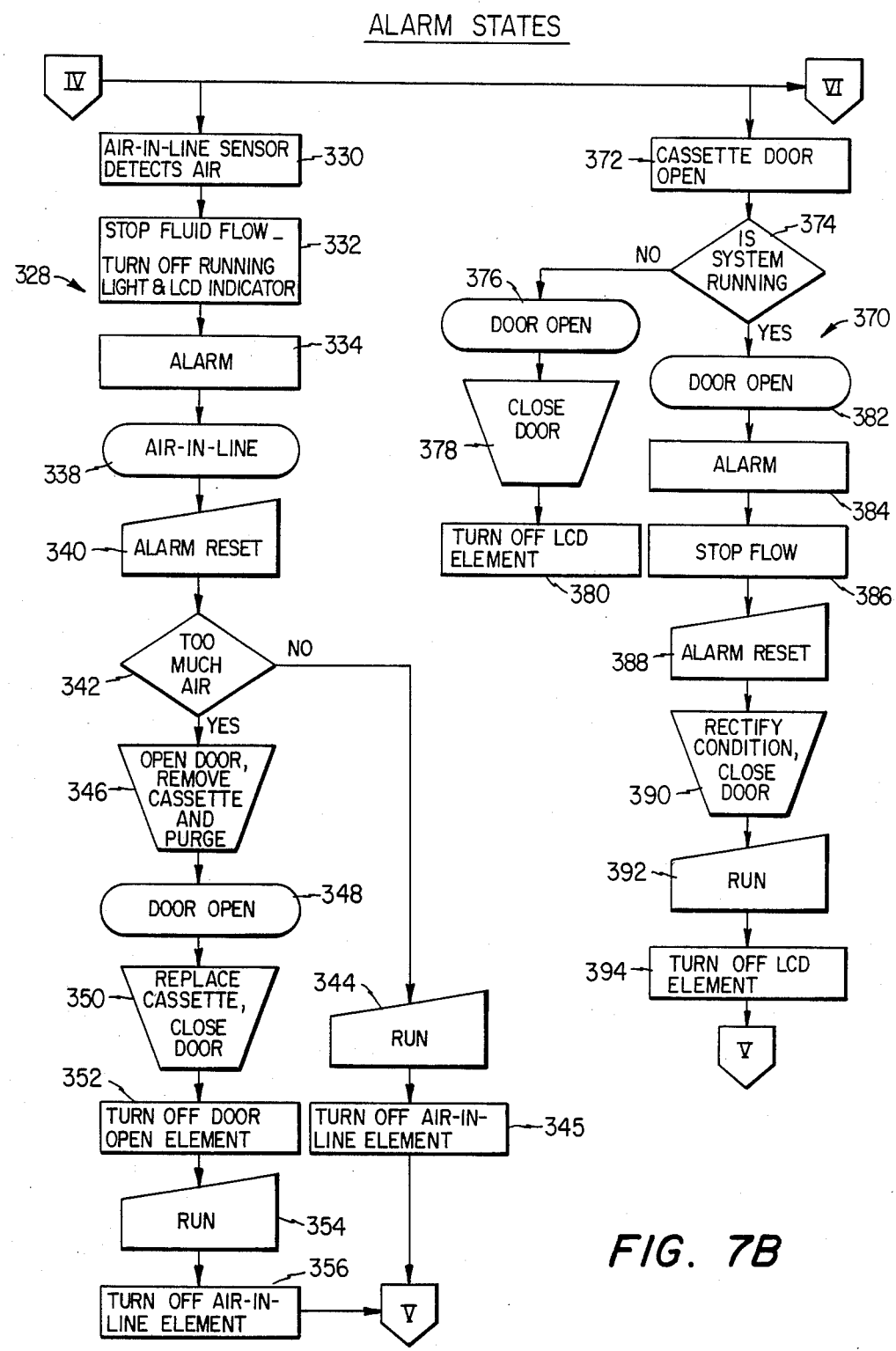

The components of controller 34 are diagrammatically illustrated in FIG. 3. A microprocessor based control unit 44 is provided. A keyboard 45 communicates with the control unit 44 through a control unit/keyboard interface 46. A display panel 48 interacts with the control unit 44 through a control unit/display panel interface unit 50. Control unit 44 communicates with the cassette operating mechanism 52 which controls operation of the cassette 40. The control unit 44 directs the operation of the cassette 40 through mechanism 52 and the mechanism 52 provides information to the control unit as to the flow metered through the cassette 40. An alarm 53 and a memory 54 are associated with the control unit 44. Various alarm sensors are also connected to control unit 44: battery condition sensor 55, door open sensor 56, air-in-line sensor 57 and occlusion sensor 58.

Door open sensor 56 senses when the door 41 covering the cassette 14 is ajar. Air in line sensor 57 senses when air has entered the fluid flow line at the position of the sensor 57 to prevent entry of air into the veins of the patient. Occlusion sensor 58 which informs the control unit when a blockage has occurred which stops or substantially slows fluid through the delivery system 10. Battery condition sensor 55 operates when the unit is in d.c. operating mode to advise of battery weakness. Alarm 53 is provided and controlled by control unit 44 to inform the operator of an emergency situation. When any of the alarm sensors 55-58 is activated, control unit 44 turns on alarm 53 to sound an audible alarm and flash the appropriate alarm legend described below.

Display section 42 includes keyboard 45 and a display panel 48. Display panel 48 includes a dual container display section 59, a dual flow line display section 60, an instruction legends section 61, and an alarm legends section 62.

Keyboard 45 is provided with ten keys 64 corresponding to the numerals 0-9 for input of data to keyboard. Enter button 66 is provided for entry of the data. A clear key 68 is provided for erasing current data to make corrections. Other keys provided, the function of which will be discussed below are: run key 70 bearing run light 72; hold key 74; alarm reset key 76; V.T.B.I. (volume to be infused) recall key 78; primary set up key 82; and secondary set up key 84. Each of the keys on keyboard 45 enter data or commands into the control unit 44 through interface 46.

Dual container display 59 of display panel 48 includes a graphic representation of a primary fluid container 86 and a graphic representation of a secondary fluid container 88. Primary fluid container representation 86 is presented so as to be readily distinguishable visually from the secondary fluid container representation 88. In the preferred form illustrated, representation 86 depicts a larger container, and extends below the bottom of representation 88, both suggestive of typical physical and spatial relationship of the actual containers 12 and 14. The words "primary" and "secondary" identifying each representation are positioned above representations 86 and 88.

In the preferred embodiment of the invention, the container representations 86 and 88 are the only portions of display panel 48 which are provided in visible form at all times for the viewer. All other elements of information, legends, data or other display on display panel 48 are provided by light means so as to be visible only when and if directed by control unit 44 through interface 50.

Associated with primary container representation 86 is a primary infusion data section 90, preferably located within representation 86. Infusion data section 90 includes a numerical register 92 accompanied by the legend "rate" 94, and a second numerical register 96 accompanied by the legends "volume . . . infused" 98, and "to be" 100, each of which is separately controlled by control unit 44. Thus, the legends 98 and 100 may be selectively activated to read either "volume infused" or "volume to be infused."

Similarly associated with secondary container representation 88 is a secondary infusion data section 104, preferably located within representation 88. Infusion data section 104 includes a numerical register 106 accompanied by the legend "rate" 108, and a second numerical register 110 accompanied by the following separately controlled legends: "volume . . . infused" 112, and "to be" 114.

Thus, each container representation has means for graphical presentation of the desired infusion data for that particular container associated therewith. Although in this form the desired infusion data is presented in the form of desired volume and rate, it could be presented as desired volume and desired time of infusion.

Dual flow line display section 60 includes primary flow line display 118 depending from primary container display 86 and secondary flow line display 120 depending from secondary container display 88. Flow line displays 118 and 120 meet in the central area of section 60 and combined flow line display 122 proceeds downwardly from their point of joinder. Primary flow line display 118 is composed of a repeating series of three discretely controlled segments 124, 126 and 128. Likewise, secondary flow line display 120 is formed by a repeating series of three discretely controlled segments 130, 132 and 134. In like manner, combined flow line display 122 is formed by repeating segments 136, 138 and 140. The commonly numbered segments (1, 2 or 3) in each flow line 118, 120 and 122 are controlled together. At any moment for an activated flow line, all of the segments in that flow line representation bearing the same index number (1, 2 or 3) will be activated, followed in sequence by the next numbered segments; i.e.: 1, 2, 3, 1, 2, 3, etc. This animation effect creates an illusion of flow.

Instruction legends section 61 consists of a series of discretely controlled legends which are activatable by control unit 44 to prompt the operator as possible. The legends are as follows:

| Reference Numeral | Legend |
| --- | --- |
| 141 | Set Primary |
| 142 | Set Secondary |
| 143 | Rate |
| 144 | Volume to be infused |
| 145 | And Push Enter |
| 146 | Or Start Infusion |
| 147 | Incorrect Entry |
| 148 | Keep Open Rate |

Alarm legends section 62 likewise contains several discrete message legends for activation by the control unit 44:

| Reference Numeral | Legend |
| --- | --- |
| 150 | Air-In-Line |
| 151 | Low Battery |
| 152 | Door Open |
| 153 | Occlusion |
| 154 | Infusion Complete. |

Figure 2B:
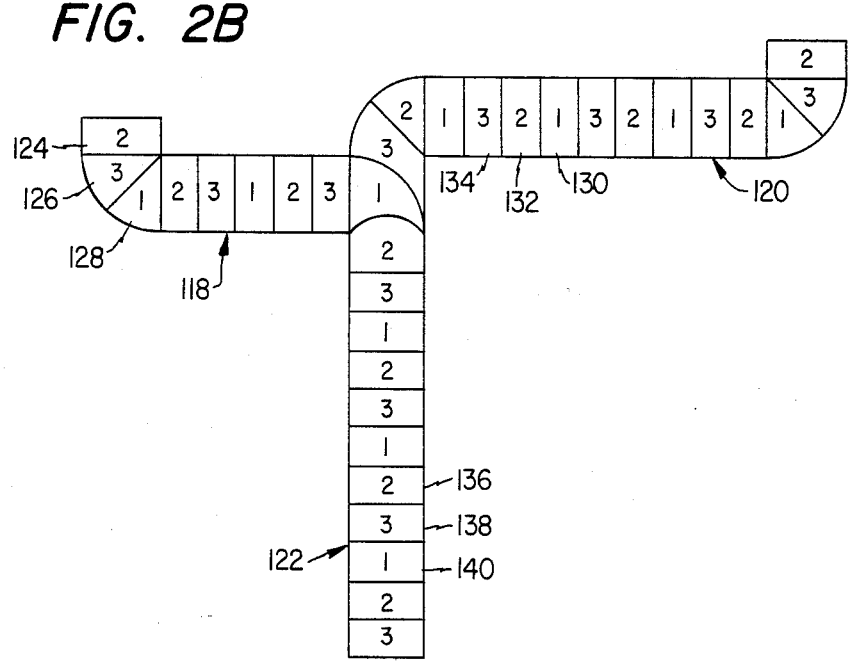
FIG. 2B illustrates detail of the fluid flow line displays on the controller.

The operation of the controller 34 is best described with reference to the logic flow charts illustrated in FIGS. 4–9 and with reference to the display section 42 illustrated in FIGS. 2A and 2B. FIGS. 4–6 illustrate the normal operation of the controller. The operator must initially provide power to the controller as represented by keyboard input 164, preferably by a switch (not shown) located behind door 41. Typically, the cassette 40 will not yet be installed and the door 41 will be open. This will cause the control unit 44 to display a "door open" legend 152 on display 48 as represented by prompt or alarm action 166, informing the operator that the door is open. The operator will then insert a cassette 40 into the controller 34 and close the door 41, as represented in the operator action 168. The control unit 44 senses the closure of the door through door open sensor 56 and turns off the "door open" legend 152 in control unit action 170.

The control unit 44 then proceeds to zero the primary and secondary volume infused registers in the memory 54. The control unit 44 also enables the keyboard 45 and commands the display to illuminate the primary "rate" legend 94 and corresponding numerical display 92, both associated with primary container representation 86 on display 48. These control unit activities are represented by control unit action 175. The display 48 is then activated to illuminate the "set primary," "rate," and "and push enter" legends 141, 143 and 145, in the instruction section 61, as shown in prompt or alarm action 176. The instruction section 61 thus prompts the operator to "set primary rate and push enter."

At this point, the operator enters the desired primary flow rate by means of the numeric keys 64, and presses enter key 66, as represented by keyboard input 178, to cause the desired primary flow rate to appear in display 92. The control unit 44 then directs the display 48 to display the "set primary," "volume to be infused" and "and push enter" displays 141, 144 and 145, in instruction section 61, as represented by prompt or alarm action 180. The control unit 44 then directs the display 48 to activate volume register display 96 and the "volume to be infused" legends 98 and 100 associated with primary container representation 86, in control unit action 182. The operator enters the desired volume and pushes the enter button 66 as represented by keyboard input 186, to cause the desired volume to be entered in display 96.

The operator now has the option to press either the run button 72 or the secondary setup button 84, depending upon whether a single fluid infusion is desired on the one hand or, on the other, a secondary fluid is to be administered. The display 48 illuminates the "set secondary" display 142, and the "or start infusion" display 146 as represented by prompt or alarm action 188. If the operator presses the run button 70, as represented by keyboard input 195, the control unit 44 will initiate infusion of the primary fluid at the selected flow rate until a volume equal to the selected volume to be infused has been metered through cassette 40. The display 92 will continuously display the rate during the infusion. The display 96 will, at all times during infusion, display the instantaneous volume of fluid already metered through controller 34, together with the legend "volume infused" 98.

If no secondary flow is desired, the value S=0 as shown in control unit action 214. The control unit 44 will then operate to cease display of the legend "to be" 100, leaving on the "volume infused" legend 98. The control unit 44 will then display on the primary volume infused display 96 the instantaneous volume of primary fluid delivered to the patient. In addition, the control unit 44 will operate the primary fluid flow line display 118 shown in FIG. 2B by sequentially activating and deactivating the individual displays 124, 126 and 128 forming the flow line display 118 to represent flow out of the primary container. The combined fluid flow line display 122 also contains three display elements, 136, 138 and 140. These elements will also be sequentially activated and deactivated to represent flow to the patient through the combined fluid flow line. The operator can therefore see an indication that flow is coming from the primary container 12 to the patient. In addition to the motion represented by flow line displays 118 and 122, running light 72 will flash repeatedly to inform the operator that the controller is operating. During infusion, the keyboard 45 is disabled. All of these control unit operations are represented by control unit action 231. An important feature of the controller is the display during primary fluid infusion of only the primary fluid flow rate and volume and the flow displays 118, 122 and light 72 during infusion. The operator is immediately aware of which fluid is being infused and is not distracted by extraneous information.

The primary fluid will be infused at the selected primary rate until the total fluid infused equals the primary volume to be infused as illustrated in control unit action 236. Upon delivery of the primary fluid volume to be infused, the control unit stops infusion and sets off the alarm 53 and "infusion complete" display 154 to indicate to the operator that the infusion is complete. The alarm will only be deactivated when the operator presses the alarm reset button 76. After delivery of the volume to be infused of primary fluid, a small infusion rate can be programmed into the system to keep the vein open for additional infusion at a later time by continuing flow from the primary container at a low rate. If the keep open rate is used, a "keep open rate" display 148 appears.

If both a primary and secondary fluid are to be delivered, the operator presses the secondary setup button 84 upon occurrence of prompt action 188, as represented by keyboard input 199. The control unit 44 will zero the secondary volume infused register, as represented by control unit action 201. The "set secondary," "rate" and "and push enter," displays 142, 143, and 145 are activated, as represented by prompt or alarm action 191. Control unit 44 proceeds to activate the secondary rate numerical display 106 and the "rate" legend 108 as represented by control unit action 192. The operator then enters the secondary rate into keys 64 and presses the enter button 66, represented by operator action 194. The control unit 44 will set the function S=1 as shown in the control unit action 200. This will direct the display 48 to display the "set secondary," "volume to be infused" and "and push enter" displays 142, 144 and 145, as represented by prompt or alarm action 202. The control unit directs the secondary volume display 110 and secondary volume legends "volume to be infused" 112 and 114 to be activated, as represented by control unit action 208. The operator then enters the desired secondary fluid volume to be infused through the keys 64 and presses the enter button 66, as represented by operator action 210.

At this stage in the operation of the controller to infuse two fluids, the relevant information for the primary rate and volume and secondary rate and volume have been entered. The control unit 44 will then prompt the operator to initiate infusion by display of only the words "start infusion" (independently activated) in display 146 as represented by prompt or alarm action 212. The operator will then depress the run button 70 as represented by operator action 216.

Where both a primary fluid and secondary fluid flow are to be delivered, the secondary fluid will be delivered first. The controller will initially stop display of the legend "to be" 114 to leave on "volume infused" display 112. The primary rate display 92 and legend "rate" display 94 and primary volume to be infused display 96 and legends "volume to be infused" 98 and 100 will also be deactivated to avoid confusion of the operator. The secondary fluid flow line display 20 and the combined fluid flow line display 122 will become activated. The secondary fluid flow line display 120 includes display elements 130, 132 and 134 which again flash sequentially to simulate flow from the secondary container to the patient. The running light 72 will also flash. In addition, the keyboard 45 is disabled. These actions are represented by the control unit action 252 in FIG. 6.

The controller then proceeds to control flow through the cassette 40 to a rate equal to the desired secondary fluid infusion rate until the total flow through the cassette equals the secondary fluid volume to be infused. Secondary volume display 110 shows the instantaneous volume of fluid metered so that the operator can observe how much fluid has been infused. The secondary rate display 106 continues to display the rate to remind the operator.

As set forth hereinabove, the secondary fluid will be infused before the primary fluid because the hydrostatic head of the secondary fluid keeps check valve 30 closed, preventing flow of the primary fluid. Therefore, if the volume of secondary fluid in the secondary container 14 is equal to the volume to be infused, the secondary container will empty precisely when the controller 34 has metered the desired secondary fluid volume to be infused and the infusion of primary fluid will begin. However, it is common to overfill such secondary containers by 10% to 15%. This will cause the overfill amount to be infused at the primary fluid rate. However, this is rarely a problem as the critical factor is usually to deliver at least the desired quantity of secondary fluid within a set time limit. The flow rate and quantity input of primary fluid is typically less critical.

When the infusion at the secondary fluid flow rate is completed, all displays and legends on the secondary container display will be deactivated. The primary fluid rate display 92 and legend "rate" 94 and primary fluid volume register 96 and legend "volume infused" 98 will be turned on. The logic value of S will be reset from 1 to 0. These actions are represented by control unit action 254. Upon completion of control unit action 254, infusion of the primary fluid occurs at the primary fluid flow rate until the primary fluid volume to be infused is achieved as represented by control unit actions 236 and 242. Displays are maintained as in primary fluid flow described above. When infusing either at the primary or secondary fluid flow rate, the controller displays only information regarding the actual fluid rate being infused, again avoiding operator confusion.

The alarm logic is illustrated in FIGS. 7A, 7B, 7C and 8. When the primary fluid infused equals the primary fluid volume to be infused, the controller will enter the infusion complete alarm condition 256. This comparison is illustrated as control unit action 258. To maintain a keep vein open flow rate (KVO flow) the controller maintains a set rate of flow through the cassette, typically 10 cc per hour, as represented by the control unit action 260. The control unit will also activate the legend "keep open rate" display 148 to inform the operator, as represented by prompt or alarm action 262.

The alarm 53 will then be activated as represented by control unit action 264. The controller activates the "infusion complete" legend 154 as represented by prompt or alarm display 266. To stop the alarm, the operator must manually push the alarm reset button 76 as represented by operator action 268.

At this point, the operator has three options: to turn off the controller, reset the system or continue the keep open flow. If the operator wishes to shut off the controller, a power on/off switch (not shown) will be activated to shut down the controller as represented by operator action 270. If the operator wishes to reset the controller, the operator will depress the primary setup button 82 as represented by keyboard input 273. The control unit will turn off the legends 148 and 154, as represented by control unit action 275, and return in a loop to the logic illustrated in FIG. 4 denoted by the arrow A for resetting the primary and secondary fluid delivery rates and volumes as desired. The third option is to push the run button 72, as represented by keyboard input 276. The control unit will then disable the alarm reset button 76 and maintain the keep open rate. The control unit totalizes the flow delivered to inform the operator of the total keep vein open flow. The sensing of an occlusion or air-in-line condition will immediately cease the infusion. These actions are represented by control unit actions 274 and 278.

An occlusion alarm condition 290 is provided. An occlusion is sensed by detecting inadequate motion of the flexible diaphragm within the cassette 40. A mechanism by which the motion may be sensed is described in U.S. patent application Ser. No. 258,362, filed Apr. 28, 1981, which disclosure is incorporated by reference herein. This action is represented by control unit action 292. If inadequate motion is sensed, the control unit 44 sets the arbitrary time function T to 0 and enters a slow alarm condition as represented by control unit action 294. The conrol unit will cause the display of the "occlusion" legend 153 as represented by prompt or alarm action 298. If, in fact, the membrane is moving, as represented by control unit decision 300, the control unit will cease the alarm condition as represented by control unit action 302 in FIG. 8 and proceed with infusion by entering the running condition logic at either point B or point C, depending upon whether both primary and secondary flow is desired or whether only primary flow is desired or remaining in the infusion condition.

If the membrane is not moving, the control unit will remain in a loop, including control unit actions 300 and 304, until the value of T exceeds two minutes. A two minute delay is provided to prevent an alarm everytime a short time occlusion occurs, for example, if the patient rolled over onto the flow line to constrict it for a short period. When this time limit is reached, the alarm will be activated and the controller will set a flow rate through the cassette 40 equal to a keep open rate, such as 10 cc per hour, as illustrated in the control unit action 306. The activation of the keep open rate will be made known to the operator by the display of the "keep open rate" display 148 as represented by prompt or alarm action 307.

At this point, the operator must press the alarm reset button 76, rectify the flow occlusion problem and press the run button 70 to reestablish normal infusion as represented by keyboard inputs and operator action 308, 310 and 312. Upon completion of these keyboard inputs and operator action, the control unit deactivates the occlusion display 153 as represented by control unit action 314, deactivates the alarm condition as represented by control unit action 302 and reinitiates infusion.

The IV delivery system 10 can be provided with an air-in-line sensor 57 along a fluid flow line to detect when air is in the flow line. It can be fatal for a patient to have air enter his veins. Therefore, an air-in-line alarm condition 328 is provided. Upon sensing of air in a fluid line, the sensor 57 communicates with the control unit 44 as represented by control unit action 330. The control unit instantly stops flow through the cassette 40 and deactivates all fluid flow line displays (118, 120 and 122) and the running light 72 as represented by control unit action 332. The alarm 53 is then sounded as represented by control unit action 334 and the legend "air-in-line" display 150 is activated as represented by prompt or alarm action 338. This prevents any air from entering the vein of the patient.

To reinitiate infusion, the operator must press the alarm reset button 76 as represented by operator action 340. The air can still be retained in the flow line. The control unit therefore reevaluates the content of air in the flow line as represented by control unit decision 342. If the air has been eliminated, the operator can depress the run button 70 to reinitiate flow as represented by keyboard input 344. The control unit will stop display of the "air-in-line" display 150, as represented by control unit action 345. If too much air remains, the operator will be required to open the door 41, remove the cassette 40 and purge the cassette and flow lines of air as represented by operator action 346. When the door is open, the control unit will automatically activate the "door open" display 152 as represented by prompt or alarm action 348. The operator will then replace the set and close the door as represented by operator action 350. The control unit senses the closure of the door and deactivates the display 152 as represented by control unit action 352. The operator can then reinitiate operation of the controller by pushing the run button 70 as represented by the operator action 354. The control unit deactivates the "air-in-line" display 190 and reinitiates infusion as represented by control unit action 356.

The cassette door alarm condition 370 is operative whenever door 41 is open. The door open sensor 56 communicates the open door information to the control unit 44 as represented by control unit action 372. The control unit then determines whether the controller is operating as represented by control unit decision 374. If not, the control unit activates the "door open" display 152 as represented by prompt or alarm condition 376 until the operator closes the door, represented by operator action 378. The display 152 is then deactivated as illustrated in control unit action 380.

If the door is open and the controller is operating, the "door open" display 152 will also be activated as represented by prompt and alarm condition 382 and the alarm 53 will also be activated as represented by control unit action 384. The control unit also stops flow through the cassette 40 as illustrated by control unit action 386. The operator must press the alarm reset button 76, rectify the open door condition, and press the run button 70 before flow can again proceed. These steps are represented by keyboard inputs and operator action 388, 390 and 392. The control unit then turns off the display 152 as represented by control unit action 394 and reinitiates infusion.

It will be desirable to provide a battery to operate the controller in the absence of external power. This will permit the patient to be moved about the hospital without the need to remove the IV delivery system and stop infusion. The controller will include a battery condition sensor 55 for detecting the remaining power reserve in the battery. The battery alarm condition 404 is activated when the sensor 55 senses a battery charge of less than 24 hours as represented by control unit action 406. The control unit will activate the "low battery" display 151 as represented by prompt or alarm condition 410. The operator's attention can be attracted to the low battery condition by flashing the flow line displays 118, 120 and 122 at a constant rate, for example, every two seconds for a one quarter to one half second display as illustrated by control unit action 412.

The reset conditions are illustrated in FIG. 9. A reset will be necessary every time a new primary or secondary container is hung and whenever a different flow rate is desired. The reset will also be necessary after each alarm condition. If a new secondary container is to be hung, as represented by control unit action 420, the operator will push the secondary setup button 84 as represented by keyboard input 422. This action will cause the control unit to stop infusion and deactivate all flow line displays, as well as running light 72, as represented by control unit action 424. The control unit will also zero the secondary fluid volume to be infused display 110 and rate display 106. The desired secondary fluid rate and volume can then be input into controller 34 to infuse the secondary fluid as described hereinabove.

If a new primary container is hung, as represented by control unit action 428, the operator will push the primary setup button 82 as represented by keyboard input 430. The control unit will again stop infusion and deactivate the flow line displays and running light 72 as represented by control unit action 432. The operator can then set in the primary fluid flow rate and volume and secondary fluid flow rate and volume as described hereinabove.

With the creation of alarm condition, represented by control unit action 433, the control unit will turn on the appropriate alarm 53, which can comprise both a visual and an audible alarm and enable the alarm reset button 76 as represented by control unit action 434. The operator will then be required to push the alarm reset button 76 as represented by keyboard input 436. The control unit will then turn off both audible and visual alarms and continue in the appropriate alarm mode as represented by control unit actions 438 and 440 until the alarm condition is alleviated.

Several additional features can be provided in controller 34. For example, if the operator wishes to recall the flow rates and volumes entered into the controller, the volume to be infused (V.T.B.I) recall button 78 can be depressed and the information will appear on displays 92, 96, 106 and 110, even while infusion is occurring.

The operator can manually stop infusion by depressing the hold button 74, and reinitiate infusion by pressing the run button 70. Also, an error in input data for flow rates and volume can be signalled by the "incorrect entry" display 147 and corrected by pressing the clear button 68 and entering the data properly.

It can be readily seen that the controller 34 is capable of delivering predetermined quantities of the primary and secondary fluids at predetermined flow rates entered by the operator. The logic of the controller simplifies the operation and provides prompting messages to the operator to inform the operator of the next step necessary to program or operate the controller. The display of the controller communicates simply and directly the significant information on the status of the system at all times. The opportunity for operator confusion or error is minimized.

Although only one embodiment of the present invention has been illustrated in the accompanying Drawings and described in the foregoing Detailed Description, it will be understood that the invention is not limited to the embodiments disclosed, but is capable of numerous rearrangements, modifications and substitutions of parts and elements without departing from the scope and spirit of the invention.

I claim:

1. An apparatus for use in the infusion into a patient of a primary fluid from a primary container and a secondary fluid from a secondary container, the secondary fluid being infused at a first predetermined rate, such rate continuing until a predetermined volume of fluid is infused and the primary fluid sequentially being infused at a second predetermined rate, said apparatus comprising:

container display means providing a visible representation of the primary and secondary containers;
    infusion data display means for displaying a first display, in association with the visible representation of the secondary container, of the first predetermined rate and instantaneous infusion data for fluid infused at the first predetermined rate, and for displaying a second display, in association with the visible representation of the primary container, of the second predetermined rate and instantaneous infusion data for fluid infused at the second predetermined rate, said infusion data display means displaying only the first display while fluid is being infused at the first predetermined rate, and only the second display while fluid is being infused at the second predetermined rate; and
    flow activation display means for generating a visible indication of the activation of fluid flow from the primary and secondary containers to the patient.

2. The apparatus of claim 1 further comprising prompting display means for sequentially prompting an operator to select the predetermined rate for the primary and secondary fluids and the predetermined volume of secondary fluid to be infused.

3. The apparatus of claim 2 further comprising means for entry by the operator of data representing the predetermined rates for the primary and secondary fluids and the predetermined volume of secondary fluid to be infused subsequent to prompting by said prompting display means.

4. The apparatus of claim 1 wherein said infusion data display means displays the flow rate and instantaneous infusion data of a fluid within the representation of the fluid container generated by said container display means.

5. The apparatus of claim 1 wherein said flow path activation display means further includes a primary flow line display representing fluid flow from the primary container and a secondary fluid flow line display representing fluid flow from the secondary container, each fluid flow line display having a plurality of discrete displays activable in a sequence to represent fluid flow.

6. The apparatus of claim 1 wherein said infusion data display means further permits an operator to select simultaneous display of the predetermined flow rates for the primary and secondary fluids and the predetermined volume to be infused for the secondary fluid during infusion of the fluids.

7. The apparatus of claim 1 further including an occlusion alarm display, sensor means for sensing an occlusion of the fluid flow path to the patient, an alarm and control means for activating the occlusion alarm display and the alarm upon sensing of an occlusion by said sensor means.

8. The apparatus of claim 1 further including an air-in-line alarm display, sensor means for sensing the presence of air in the fluid flow path to the patient, an alarm and control means for stopping infusion and activating the air-in-line alarm display and the alarm upon sensing of air by said sensor means.

9. An apparatus for controlling the infusion of a the primary fluid from a primary container and a secondary fluid from a secondary container to a patient, the secondary fluid being metered through the apparatus at a predetermined secondary flow rate until a predetermined volume of fluid is metered, fluid subsequently being metered through the apparatus at a predetermined primary fluid rate to deliver the primary fluid from the primary container to the patient, the primary fluid from the primary container flowing through a primary fluid flow line and the secondary fluid from the secondary container flowing through a secondary fluid flow line, said apparatus comprising:

display means for generating visible representations of the primary and secondary containers and said display means further for representing the flow rate and volume to be infused for the primary and secondary fluids in association with the representation of said primary and secondary containers, respectively;

means for entry of data representing the predetermined flow rate and volume to be infused for both the primary and secondary fluids;

prompting display means for displaying prompting instructions to prompt the operator to enter the predetermined primary and secondary flow rates and volumes to be infused;

flow line activation display means for representing activation of fluid flow through the primary and secondary flow lines;

control means for controlling said prompting display means to sequentially display selected prompting instructions to prompt the operator to enter the flow rate and volume to be infused for each of the primary and secondary fluids through said means for entry of data, said control means further for controlling the flow line activation display means to represent activation of the secondary fluid flow line during metering at the predetermined secondary flow rate and subsequently to represent activation of the primary fluid flow line to indicate the fluid being infused to the patient, said control means further for displaying the secondary flow rate and fluid volume metered through the apparatus at the secondary flow rate on said display means in association with the representation of the secondary container while fluid is metered therethrough at the secondary fluid rate and subsequently displaying on said display means in association with the representation of the primary container, the primary fluid rate and volume metered through the apparatus at the primary flow rate during metering of fluid at the primary fluid rate.

10. The apparatus of claim 9 wherein said display means displays the flow rate and volume of fluid metered through the apparatus within the representation of the fluid container generated by said display means.

11. The apparatus of claim 9 wherein said flow line activation display means further includes a primary fluid flow line display for representing fluid flow from the primary container to the patient and a secondary fluid flow line display for representing fluid flow from the secondary container to the patient, each fluid flow line display having a plurality of discrete displays activatable in a sequence to represent fluid flow.

12. The apparatus of claim 9 wherein said display means represents the flow rate and volume metered through the apparatus for only the fluid flow rate being utilized at the time.

13. The apparatus of claim 9 wherein said display means further provides for an operator to elect simultaneous display of the predetermined flow rates for the primary and secondary fluids and the primary and secondary fluid volumes to be infused during infusion of the fluids.

14. The apparatus of claim 9 further including an occlusion alarm display and sensor means for sensing occlusion of the fluid flow path between the first and second fluid containers and the patient, said apparatus further comprising an alarm, said control means activating the alarm and the occlusion alarm display upon sensing by the sensor means of an occlusion after a predetermined time interval delay to prevent an alarm for a short time occlusion.

15. The apparatus of claim 9 further comprising an air-in-line alarm display and sensor means for sensing the presence of air in the fluid flow between the first and second fluid containers and the patient, said apparatus further comprising an alarm, said control means for stopping infusion and activating the air-in-line alarm display and the alarm upon sensing of air by said sensor means.

16. A method for use in association with an apparatus for controlling the infusion to a patient of a primary fluid from a primary container and a secondary fluid from a secondary container, the secondary fluid being infused at a predetermined secondary fluid flow rate until a predetermined volume of fluid is infused and the primary fluid subsequently being infused at a predetermined primary fluid flow rate, said method comprising the steps of:

displaying a visual representation of the primary container on a display;

displaying a visual representation of the secondary container on the display;

displaying the flow rate and instantaneous volume of fluid infused at the secondary flow rate on the display in association with the representation of the secondary container;

displaying the flow rate and instantaneous volume of fluid infused at the primary flow rate on the display in association with the representation of the primary container; and displaying a visual representation of flow from the container from which fluid is being infused to the patient.

17. The method of claim 16 further comprising the step of displaying on the display prompting messages to direct an operator to input the predetermined flow rates and predetermined volume to be infused into a keyboard.

18. The method of claim 16 wherein said step of displaying on a display a flow rate and instantaneous volume of fluid metered further comprising displaying the flow rate and instantaneous volume metered of only the fluid being metered at the instant of display; and said step of displaying a visible representation of a flow including the steps of displaying on the display visible representations of a primary fluid flow line extending from the primary container, a secondary fluid flow line extending from the secondary container and displaying a visible representation of fluid flowing through the fluid flow line representation representing the flow line in which fluid is flowing to the patient.

19. The method of claim 16 further comprising the steps of sensing an occlusion of the fluid flow path between the fluid containers and the patient, and activating an occlusion alarm display and generating an alarm to inform the operator upon sensing an occlusion.

20. The method of claim 16 further comprising the steps of sensing the presence of air in the fluid flow between the fluid container and the patient, and activating an air-in-line alarm display, stopping infusion, and generating an alarm upon sensing of air.

21. The method of claim 16 wherein said steps of displaying the rate and volume of fluid infused further comprise the steps of displaying the rate and volume of fluid infused within the visual representation of the container containing the fluid.

22. The method of claim 16 further comprising the step of momentarily displaying the predetermined rates and volumes to be infused for both fluids upon request by the operator.

23. A method for use in association with an apparatus for controlling the infusion to a patient of a primary fluid from a primary fluid container and a secondary fluid from a secondary fluid container, the apparatus metering the secondary fluid to the patient at a predetermined first flow rate until a volume is infused equal to a predetermined first fluid volume to be infused and subsequently metering fluid to the patient at a predetermined second flow rate until a volume is infused equal to a second predetermined fluid volume to be infused, comprising the steps of:
displaying on a display visible representations of the primary and secondary fluid containers;
displaying prompting messages on the display to direct an operator to input the predetermined first flow rate, the predetermined first volume to be infused, the predetermined second flow rate and the predetermined second volume to be infused into a keyboard, the input information for the first flow rate and first fluid volume to be infused being displayed in association with the representation of the secondary fluid container during input of the information and the input information for the second flow rate and second fluid volume to be infused being displayed in association with the representation of the primary fluid container during input of the information;
displaying on the display in association with the representation of the secondary container the first flow rate and the instantaneous volume of fluid metered through said apparatus while fluid is metered through said apparatus at the first flow rate;
displaying on the display in association with the representation of the primary container the second flow rate and instantaneous volume of fluid metered through said apparatus at the second flow rate; and
displaying on the display a representation of a primay fluid flow line extending from the primary container for fluid delivery to the patient and a secondary fluid flow line extending from the secondary container for fluid delivery to the patient and visually representing flow through the representation of the secondary fluid flow line during metering at the first flow rate to represent the flow of fluid from the secondary container and visually representing flow through the representation of the primary fluid flow line during metering at the second flow rate to represent flow from the primary container to provide a visual indication of the fluid being infused.

24. The method of claim 23 further comprising the steps of sensing an occlusion of the fluid flow path between the primary and secondary containers and the patient and activating an occlusion alarm display and producing an alarm to inform the operator of the occlusion upon sensing of an occlusion.

25. The method of claim 23 further comprising the steps of sensing the presence of air in the fluid flow path from the primary and secondary containers to the patient and activating an air-in-line alarm display, producing an alarm and stopping the metering of fluid upon sensing of air.

26. The method of claim 23 wherein the steps of displaying on the display the fluid flow rates and instantaneous volume of fluid metered through the apparatus further comprise the step of displaying the flow rate and instantaneous volume of fluid metered through the apparatus within the visible representations of the containers containing the fluids.

27. The method of claim 23 further comprising the step of momentarily displaying the predetermined flow rates and volumes to be infused for each fluid during infusion upon request by the operator.

28. The method of claim 23 wherein said steps of displaying the flow rates and instantaneous volume of fluid metered through the apparatus further comprise the step of displaying the flow rate and instantaneous volume of fluid metered through the apparatus for only the fluid being infused.

29. The method of claim 23 wherein said step of displaying a representation of a primary fluid flow line and secondary fluid flow line further comprises the step of displaying on the display a representation of a combined fluid flow line extending from an intersection of the primary and secondary fluid flow lines to the patient and visually representing flow through the representation of the combined fluid flow line during metering of fluid to the patient.

30. An apparatus for use in the infusion into a patient of a primary fluid from a primary container and a secondary fluid from a secondary container, the secondary fluid being infused at a first predetermined rate, such rate continuing until a predetermined volume of fluid is infused and the primary fluid subsequently being infused at a second predetermined rate, said apparatus comprising:
container display means providing a visible representation of the primary and secondary containers;
secondary fluid numerical display means closely associated with the representation of the secondary container;
a primary fluid numerical display means closely associated with the representation of the primary container; and
means for inputing and displaying on each of said secondary fluid numerical display means and said primary fluid numerical display means at least two of the following data for each of said fluids: selected flow rate, selected volume to be infused, selected time of infusion.

31. An apparatus for use in the infusion into a patient of a primary fluid from a primary container and a secondary fluid from a secondary container, the secondary fluid being infused at a first predetermined rate, such rate continuing until a predetermined volume of fluid is infused and the primary fluid subsequently being infused at a second predetermined rate, said apparatus comprising:

- container display means providing visible, distinguishable representations of the primary and secondary containers;
- secondary fluid flow condition display means for generating a visible display closely associated with the visible representation of the secondary container for displaying the first predetermined rate and instantaneous data indicating the status of infusion at that rate;
- primary fluid flow condition display means for generating a visible display closely associated with the visible representation of the primary container for displaying the second predetermined rate and instantaneous data indicating the status of infusion at that rate;
- means for displaying only the secondary fluid flow condition display means while fluid is being infused at the first predetermined rate and for displaying only the primary fluid flow condition display means while fluid is being infused at the second predetermined rate; and
- control means for disabling the primary fluid flow condition display means and enabling the secondary fluid flow condition display means while infusion is occurring at the first rate; and for disabling the secondary fluid flow condition display means and enabling the primary fluid flow condition display means while infusion is occurring at the second rate.

* * * * *